(12) United States Patent
Gahr et al.

(10) Patent No.: US 9,075,036 B2
(45) Date of Patent: Jul. 7, 2015

(54) METHOD FOR DETERMINING AND/OR MONITORING AT LEAST ONE PROCESS VARIABLE OF A MEDIUM, A CORRESPONDING ELECTROCHEMICAL SENSOR AND A CORRESPONDING SYSTEM

(71) Applicant: Endress + Hauser Conducta Gesellschaft für Mess- und Regeltechnik mbH + Co. KG, Gerlingen (DE)

(72) Inventors: Achim Gahr, Goldbach (DE); Torsten Pechstein, Radebeul (DE); Thomas Wilhelm, Halle (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 266 days.

(21) Appl. No.: 13/669,555

(22) Filed: Nov. 6, 2012

(65) Prior Publication Data
US 2013/0113459 A1 May 9, 2013

(30) Foreign Application Priority Data
Nov. 7, 2011 (DE) .......................... 10 2011 085 841

(51) Int. Cl.
*G01N 33/18* (2006.01)
*G01N 27/30* (2006.01)

(52) U.S. Cl.
CPC ................ *G01N 33/18* (2013.01); *G01N 27/30* (2013.01)

(58) Field of Classification Search
CPC . G01N 27/30; G01N 27/4165; G01N 27/302; G01N 27/31; G01N 27/4162; G01N 27/4167; G01N 27/301; G01N 27/4035; G01N 27/414; G01N 27/4166; G01N 33/18; A61B 5/14539; G05D 21/00
See application file for complete search history.

(56) References Cited

U.S. PATENT DOCUMENTS

| | | | | |
|---|---|---|---|---|
| 4,927,517 A | * | 5/1990 | Mizutani et al. | 204/406 |
| 6,277,267 B1 | * | 8/2001 | Geloven et al. | 205/781 |

(Continued)

FOREIGN PATENT DOCUMENTS

| | | |
|---|---|---|
| CN | 1756953 A | 4/2006 |
| CN | 1882830 A | 12/2006 |

(Continued)

OTHER PUBLICATIONS

German Search Report, Aug. 24, 2012, German Patent Office.

*Primary Examiner* — Minh N Tang
(74) *Attorney, Agent, or Firm* — Bacon & Thomas, PLLC (57) ABSTRACT

A method for determining and/or monitoring at least one process variable of a medium by the utilization of at least of an electrochemical sensor comprising at least a first reference half cell and a second reference half cell, and comprising the method steps as follows: measuring a first electrical measured variable $X_{1,cont}$ with a first measuring period $t_{1,meas}$ and a first measuring interval $t_{1,int}$ with reference to the first reference half cell; measuring at least a second electrical measured variable $X_{2,discont}$ with a second measuring period $t_{2,meas}$ and a second measuring interval $t_{2,int}$ with reference to the second reference half cell; wherein the second measuring interval $t_{2,int}$ is greater than the first measuring interval $t_{1,int}$; and determining the at least one process variable from at least one electrical measured variable $X_{1,cont}$ or $X_{2,discont}$. Furthermore, the invention relates to an electrochemical sensor and to a system.

15 Claims, 5 Drawing Sheets

(56) References Cited

U.S. PATENT DOCUMENTS

| | | | |
|---|---|---|---|
| 6,287,439 B1 * | 9/2001 | Kato et al. | 204/425 |
| 2005/0202313 A1 | 9/2005 | Franzheld | |
| 2006/0125481 A1 * | 6/2006 | Pechstein et al. | 324/426 |
| 2007/0080075 A1 | 4/2007 | Wang et al. | |

FOREIGN PATENT DOCUMENTS

| | | |
|---|---|---|
| CN | 101087993 A | 12/2007 |
| CN | 101929977 A | 12/2010 |
| CN | 102144158 A | 8/2011 |
| CN | 102147388 A | 8/2011 |
| DE | 19626277 A1 | 1/1998 |
| DE | 10243930 A1 | 9/2003 |
| DE | 10356638 A1 | 6/2005 |
| DE | 102005035511 A1 | 2/2007 |
| EP | 1219958 A1 | 7/2002 |
| EP | 2233994 A2 | 9/2010 |
| JP | 9127049 A | 5/1997 |
| WO | WO 2005/054836 A1 | 6/2005 |

* cited by examiner

METHOD FOR DETERMINING AND/OR MONITORING AT LEAST ONE PROCESS VARIABLE OF A MEDIUM, A CORRESPONDING ELECTROCHEMICAL SENSOR AND A CORRESPONDING SYSTEM

TECHNICAL FIELD

The invention relates to a method for determining and/or monitoring at least one process variable of a medium by means of an electrochemical sensor, to a corresponding electrochemical sensor and to a corresponding system.

BACKGROUND DISCUSSION

A great number of sensors are utilized for monitoring the properties of a media. Thus, for example, in the case of monitoring water quality in distribution networks, especially drinking water, at least one of the following parameters are monitored: Temperature; flow, e.g. flow rate; pressure; pH value; redox potential; oxygen, ammonium, phosphate, nitrate, nitrite and chlorine content; global parameters, especially chemical, and/or biochemical, oxygen demand; conductivity; and (dissolved) organic ingredients, especially total (dissolved) carbon and turbidity. In such case, so-called multiparameter sensors can be used. Multiparameter sensors are sensors that are able (simultaneously) to measure more than one process variable.

A distribution network in the sense of this invention is to be understood to include a (pipe-)line, silo, tank, container, water network or gas network.

Ideally, the sensors measure over a longer period of time, at least one year, without requiring maintenance and calibration. Of course, the measurements must be accurate over this period of time.

Sensors for measuring pH value, redox potential, oxygen and chlorine utilize predominantly electrochemical methods, especially potentiometric and amperometric methods. A problem at which the invention is directed will be explained here with reference to potentiometric sensors. The invention is, however, not limited to potentiometric sensors, but generally relates to sensors for use in electrochemical measuring systems. It is furthermore an option to apply the ideas of the invention to non-electrochemical sensors.

Potentiometric sensors have at least one measuring electrode and a reference electrode, between which a potential difference is determined. The potential difference is, in such case, dependent on the activity or the concentration of the substance being measured; in the case of a pH measurement, for example, dependent on the activity of the hydrogen ion H+, which, in the case of a pH measurement of a dilute solution, corresponds essentially to the proton concentration.

Besides systems comprising a measuring electrode and a reference electrode, which are introduced separately into a medium, especially in the field of pH measurement, so called single-rod measuring chains are also known, which combine measuring electrode and reference electrode in one probe. These probes comprise, as a rule, two concentrically arranged tubes, wherein the low resistance reference half cell is arranged in the outer tube, and simultaneously serves for shielding the high resistance pH half cell. Besides the described embodiment, there exist still other forms of embodiment of electrochemical sensors in thick film or thin film technology.

In all cases, at least one of the electrodes is immersed in an electrolyte, which has electrolytic contact with the medium via a liquid junction. Typically, silver/silver chloride electrodes are made use of in an electrolyte of defined chloride ion activity, as a rule 3 molar.

Especially the electrolyte of the reference electrode depletes with time via the liquid junction. This leads to a continuous drift in the measured values, and the measuring becomes inaccurate. Because of electrolyte depletion, the measured value drifts by, for instance, 0.1-0.2 mV per day. Disturbing diffusion and streaming potentials can also form, which likewise corrupt the measuring.

SUMMARY OF THE INVENTION

An object of the invention is thus to enable a durably reliable and correct measuring of parameters relevant to a distribution network.

The object is achieved by a method performed by means of at least one electrochemical sensor comprising at least a first reference half cell and a second reference half cell and comprising method steps as follows:

measuring a first electrical measured variable $X_{1,\,cont}$ with a first measuring period $t_{1,\,meas}$ and a first measuring interval $t_{1,\,int}$ with reference to the first reference half cell, measuring at least a second electrical measured variable $X_{2,\,discont}$ with a second measuring period $t_{2,\,meas}$ and a second measuring interval $t_{2,\,int}$ with reference to the second reference half cell, wherein the second measuring interval $t_{2,\,int}$ is greater than the first measuring interval $t_{1,\,int}$, determining the at least one process variable from at least one electrical measured variable $X_{1,\,cont}$ or $X_{2,\,discont}$.

It is especially advantageous that the method provides the measuring of a first electrical measured variable $X_{1,\,cont}$, and, independently thereof, a second electrical measured variable $X_{2,\,discont}$. Thus, the second measuring interval $t_{2,\,int}$ can be selected so as to be larger than the first measuring interval $t_{1,\,int}$. The process variable can be determined from at least one electrical measured variable $X_{1,\,cont}$ or $X_{2,\,discont}$. Without loss of generality, the first measuring interval $t_{1,\,int}$ can be selected, for instance, so as to be equal to the first measuring period $t_{1,\,meas}$ (i.e. continuous measuring), and the second measuring interval $t_{2,\,int}$ can be set to daily measuring. The second electrical measured variable $X_{2,\,discont}$ can be used for evaluating the quality of the measuring of the first electrical measured variable $X_{1,\,cont}$. Following this, corresponding measures can be undertaken; for instance, a recalibration, an adapting, an adjusting, a replacement, a refilling, etc.

In an advantageous embodiment, a difference electrical measured variable $X_{diff}$ is registered, with $X_{diff}(t=t_0)=K_{1,\,cont}(t=t_0)-X_{1,\,cont}(t=t_0-t_1)$, wherein t represents time, $t_0$ represents the point in time of the current measured value, and $t_1$ represents a whole numbered multiple of the measuring interval $t_{1,\,int}$, and wherein a falling of the difference electrical measured variable $X_{diff}$ below a lower threshold value $X_{1,\,min}$ or a rising of the difference electrical measured variable $X_{diff}$ above an upper threshold value $X_{1,\,max}$ means occurrence of an event, which changes the process variable.

From the electrical measured variable $X_{1,\,cont}$, a difference measured variable $X_{diff}$ is thus registered, whereby even fast changes in the process parameter can be ascertained.

Advantageously, measurement of the second electrical measured variable $X_{2,\,discont}$ is triggered, when the difference electrical measured variable $X_{diff}$ is determined to lie under the threshold value $X_{1,\,min}$ or over the threshold value $X_{1,\,max}$. In this way, via a second measuring, the measurement result can be checked and corresponding measures can be taken.

In a preferred embodiment, at least one of the electrical measured variables $X_{1, cont}$ or $X_{2, discont}$ is ascertained via a potentiometric method, wherein a component with a sensor effect is provided, which is in contact with the medium, wherein the first electrical measured variable $X_{1, cont}$ is measured relative to the component with the sensor effect, and wherein the second electrical measured variable $X_{2, discont}$ is measured relative to the component with the sensor effect or relative to the first reference half cell.

In an alternative preferred embodiment, at least one of the electrical measured variables $X_{1, cont}$ or $X_{2, discont}$ is ascertained via an amperometric method, wherein an electrode surface is provided, which is embodied as a counterelectrode.

The object is furthermore achieved by an electrochemical sensor comprising at least a first reference half cell and a second reference half cell,
wherein the first reference half cell determines a first electrical measured variable $X_{1, cont}$ with a first measuring period $t_{1, meas}$ and a first measuring interval $t_{1, int}$, wherein the second reference half cell determines a second electrical measured variable $X_{2, discont}$ with a second measuring period $t_{2, meas}$ and a second measuring interval $t_{2, int}$, wherein the second measuring interval $t_{2, int}$ is greater than the first measuring interval $t_{1, int}$,
wherein at least one superordinated unit is provided, which ascertains the at least one process variable from at least one electrical measured variable $X_{1, cont}$ or $X_{2, discont}$.

It is advantageous that the sensor includes a first reference half cell for determining a first electrical measured variable $X_{1, cont}$ and, independently thereof, a second reference half cell for determining a second electrical measured variable $X_{2, discont}$. Thus, the second measuring interval $t_{2, int}$ can be selected so as to be greater than the first measuring interval $t_{1, int}$ and the superordinated unit can determine the process variable from at least one electrical measured variable $X_{1, cont}$ or $X_{2, discont}$.

Without loss of generality, the first measuring interval $t_{1, int}$ can be selected, for instance, so as to equal the first measuring period $t_{1, meas}$ (i.e. continuous measuring), and the second measuring interval $t_{2, int}$ can be set to daily measuring. The second electrical measured variable $X_{2, discont}$ can thus be used for evaluating the quality of the measuring of the first electrical measured variable $X_{1, cont}$. The superordinated unit can then take corresponding measures; for instance, a recalibration, an adapting, an adjusting, a replacement, a refilling, etc. of the first reference half cell.

In a preferred embodiment, the superordinated unit ascertains a difference electrical measured variable $X_{diff}$ with $X_{diff}(t=t_0)=X_{1, cont}(t=t_0)-X_{1, cont}(t=t_0-t_1)$,
wherein t is time, $t_0$ represents the point in time of the current measured value, and $t_1$ represents a whole numbered multiple of the measuring interval $t_{1, int}$,
wherein the superordinated unit associates a value of the difference electrical measured variable $X_{diff}$ under a lower threshold value $X_{1, min}$ or over an upper threshold value $X_{1, max}$ with an occurrence of an event, which changes the process variable.

From the electrical measured variable $X_{1, cont}$, the superordinated unit thus ascertains a difference measured variable $X_{diff}$, whereby even fast changes in the process parameter are ascertained.

In such case, in an advantageous form of embodiment, the superordinated unit triggers measurement of the second electrical measured variable $X_{2, discont}$, when it determines that the difference electrical measured variable $X_{diff}$ lies under the threshold value $X_{1, min}$ or over the threshold value $X_{1, max}$. In this way, via a second measuring, the measurement result can be checked, and corresponding measures can be taken. Measures could be: A recalibration, an adapting, an adjusting, a replacement, a refilling, etc.

In a preferred embodiment, a component with a sensor effect is provided, which is in contact with the medium, wherein the first reference half cell ascertains the measured variable $X_{1, cont}$ relative to the component with a sensor effect via a potentiometric method, and/or
wherein the second reference half cell ascertains the measured variable $X_{2, discont}$ relative to the component with a sensor effect or relative to the first reference half cell via a potentiometric method.

In an alternative preferred embodiment, the first reference half cell ascertains the measured variable $X_{1, cont}$ and/or the second reference half cell ascertains the measured variable $X_{2, discont}$ via an amperometric method,
wherein an electrode surface is provided, which is embodied as a counterelectrode.

Advantageously, the second reference half cell includes at least one supply of electrolyte and is in contact with the medium via at least a first liquid junction,
wherein the liquid junction is embodied so as to be controllable, and the superordinated unit controls the liquid junction in such a manner, that the liquid junction is electrolytically permeable during measurement operation.

Preferably, the control interval of the liquid junction associated with the second reference half cell corresponds to the second measuring interval $t_{int2}$.

This is advantageous in that the control interval of the liquid junction can be matched to the second measuring interval $t_{int2}$. The liquid junction is varied as regards its permeability and/or its electrolyte flow, and is opened only for measuring. In this way, a depletion of the electrolyte supply of the second reference half cell as well as a contamination the second reference half cell by the medium can be greatly slowed, and the lifetime of the sensor can be increased. As already mentioned, the measurement of the second reference half cell can be used for recalibration, adapting, adjusting, etc. of the first reference half cell.

In a preferred form of embodiment, the first reference half cell includes at least one supply of electrolyte, and is in contact with the medium via at least a second liquid junction, wherein the liquid junction is embodied so as to be controllable, and the superordinated unit controls the liquid junction in such a manner that the liquid junction is electrolytically permeable during measurement operation, wherein the control interval of the second liquid junction corresponds to the first measuring interval $t_{int1}$.

Advantageously, the component with a sensor effect is a galvanic half cell, an ion-selective membrane, especially a pH glass membrane, a semiconductor insulator layer stack, especially an ISFET, a metal electrode or metal/metal oxide electrode, or a non-metallic redox electrode, especially a carbon electrode. With help of said components with a sensor effect, the object can be fulfilled, since, distribution network relevant parameters can be determined therewith.

The object is furthermore achieved by a system in a distribution network, wherein the system comprises at least two electrochemical sensors, wherein a first electrochemical sensor at a first location registers information, especially measurement data, and/or an event, at a first point in time, wherein a further electrochemical sensor or a number of other electrochemical sensors, which are arranged at at least one other location, register such information and/or event at a later point in time, and wherein a superordinated control unit detects the propagation of the information and/or of the event and triggers a procedure, especially a registering, reporting, and/or measure to be taken.

This is advantageous, in that the application of a plurality of electrochemical sensors in a distribution network allows a geometrically distributed monitoring of the network. Thus, occurring events can be detected and tracked via their progression in time and space. An option is that the event is recorded, stored and/or logged. Depending on the type of event, a corresponding measure can be taken. Thus, the superordinated unit orders, for instance, a redirecting of the flow of medium via opening/closing of gates, etc. Options include issuing a report, an alarm and the like. An event can be, for instance, a contamination, a (too) fast or (too) slow changing of a measured value, the detection of an unwanted element, a too high or too low concentration of an element, among other things.

If, in general, something unexpected or undesired occurs, this can be reacted to in a timely manner via the invention.

BRIEF DESCRIPTION OF THE DRAWINGS

The invention will now be explained in greater detail based on the appended drawing, the figures of which show as follows:

FIG. 1 a schematic representation of a first embodiment of an electrochemical sensor of the invention, FIG. 2 a difference measurement, ascertained with the electrochemical sensor of the invention, FIG. 3 a schematic representation of a second embodiment of an electrochemical sensor of the invention, FIG. 4 a schematic representation of a third embodiment of an electrochemical sensor of the invention, FIG. 5a a schematic representation of a system of the invention, and FIG. 5b a schematic representation of the time and locational progression of an event registered with the system of the invention of FIG. 5a.

In the figures, equal features are provided with equal reference characters.

DETAILED DISCUSSION IN CONJUNCTION WITH THE DRAWINGS

Figure 1:
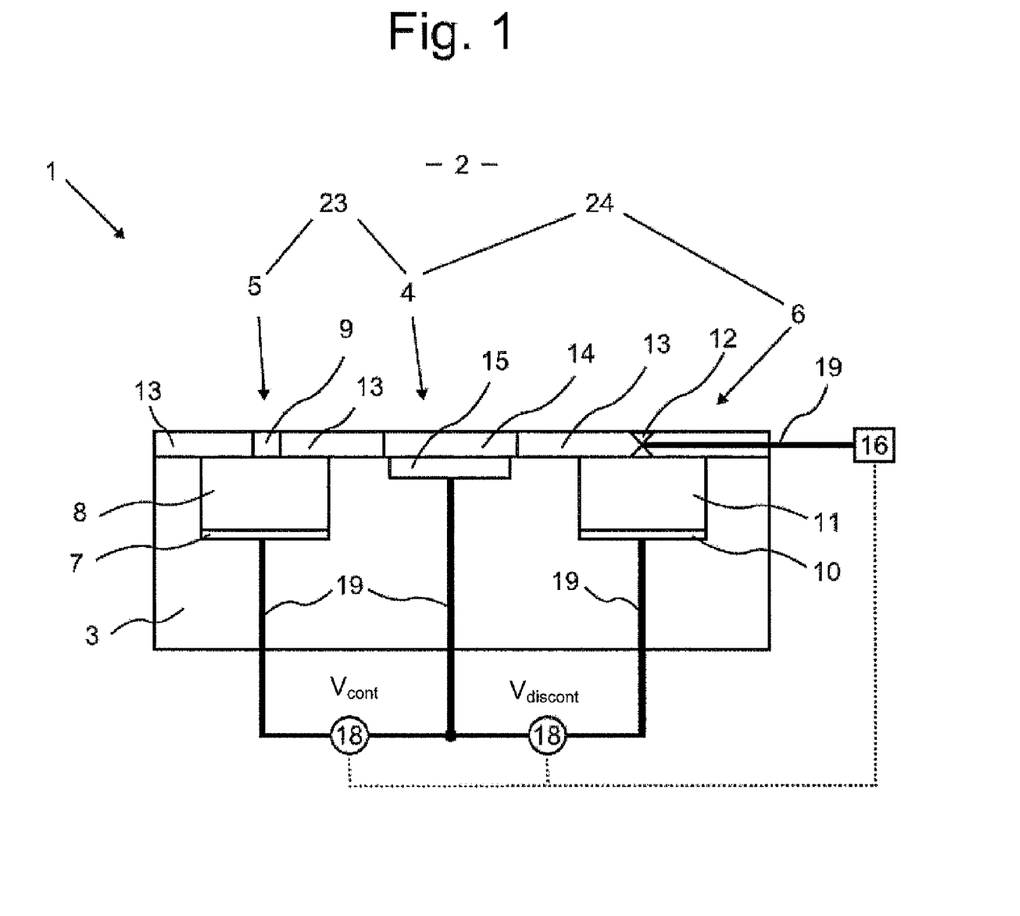

FIG. 1 shows schematically the construction of an electrochemical sensor 1 embodied according to the invention. Reference character 1 refers to the total sensor. Sensor 1 is produced in using thick film technology. An option for manufacture is, however, also thin film technology.

In the case of thick film technology, the (functional) layers are most often applied onto a carrier using screen printing followed by firing. Often in this process, additional, non-printable components are applied onto the carrier, for which reason one also speaks of thick film, hybrid technology.

In the case of thin film technology, deposition of the layers occurs, most often over the full surface of a carrier, most often a substrate made of silicon or a ceramic, with methods of physical (for instance evaporating, sputtering, ion plating or ICB (ionized cluster beam) technology), and chemical, gas phase deposition (especially also plasma-supported methods).

Figure 3:
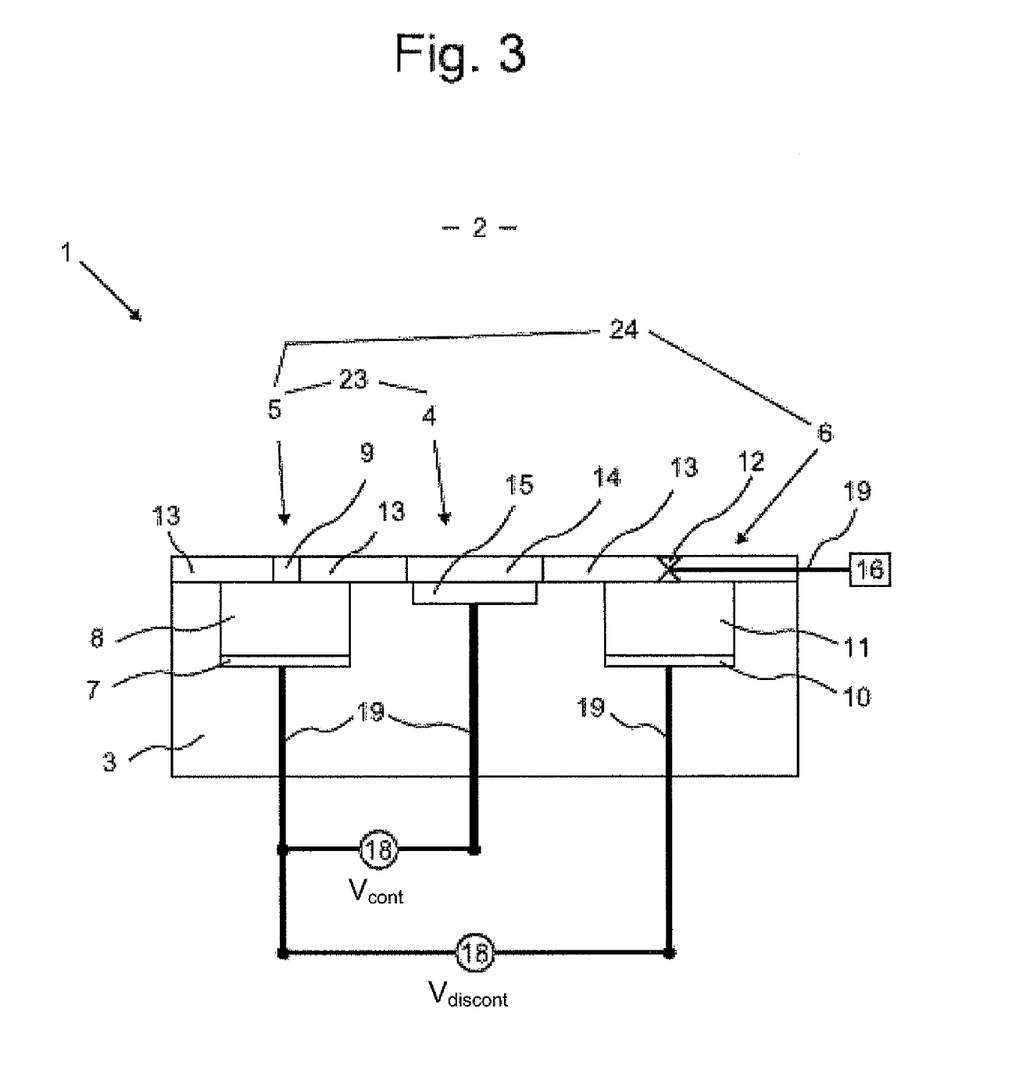
Figure 4:
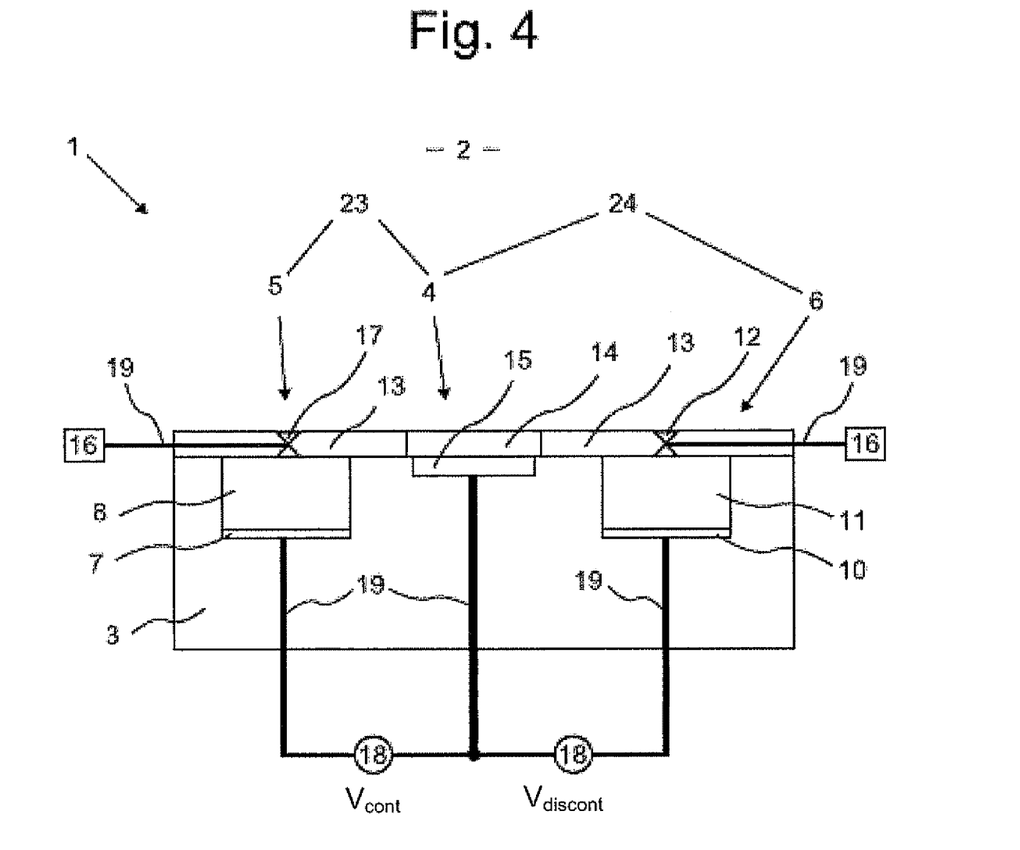

Sensor 1 includes a carrier 3, which can be a ceramic substrate, a ceramic film, a circuit board or the like, and is surrounded by a medium 2. In FIG. 1, FIG. 3 and FIG. 4, medium 2 is shown above sensor 1. Via corresponding sealing systems (not shown), certain regions of sensor 1 can be protected from the medium 2. Here, reference is especially to the region of the electrical lines 19 and, generally, the region of sensor 1 sensitive to the medium. Furthermore, sensor 1 can be installed in a distribution network, thus in a (pipe-)line, silo, tank, container, gas network, and especially in a water distribution network 20 (compare FIG. 5), and be flowed around by medium.

The solution of the invention shall be explained based on a potentiometric sensor, especially based on a pH sensor. In such case, as a rule, no electrical current flows through the electrical lines 19. The invention can, however, also be applied to electrochemical methods, in which electrical current does flow, such as, for example, in the case of the amperometry or coulometry.

Moreover, also multiparameter sensors can be used, i.e. sensors which measure more than just one process parameter. An option is also to register with the multiparameter sensor non-electrochemically determinable process variables, including, especially, temperature, conductivity, flow, pressure, or turbidity.

Sensor 1 is composed essentially of a component 4 with a sensor effect (implemented in the example as measuring half cell and shown in the center), a first reference half cell 5 and a second reference half cell 6.

FIG. 1 shows a first embodiment. The component with a sensor effect 4 thus forms with the first reference half cell 5 a first galvanic element 23 and with the second reference half cell 6 a second galvanic element 24. The first galvanic element 23 measures with a first measuring period $t_{1,\ mess}$ and a measuring interval $t_{1,\ int}$; the second galvanic element 24 measures with a second measuring period $t_{2,\ meas}$ and a measuring interval $t_{2,\ int}$.

The component with a sensor effect 4 has contact across a sensitive area 14 with the medium 2, whose pH value is to be determined. The sensitive area 14 is a pH sensitive layer and is, for example, embodied as a thin glass membrane ($\approx$50 μm). Via a lead 15, which is composed, for example, of a mixed conducting oxide layer and a gold layer, the sensitive area 14 is connected with an electrical line 19.

The first reference half cell 5 includes an electrode 7, which most often represents a silver/silver chloride electrode. Furthermore, the reference half cell 5 includes a supply of electrolyte 8, most often in the form of a potassium chloride solution. Via a liquid junction 9, the supply of electrolyte 8 is in contact with medium 2. Liquid junction 9 can be embodied as a diaphragm or a small opening. For sensing the potential, electrode 7 is connected with an electrical line 19.

The cover layer 13, also called the passivation, protects all regions of the sensor 1, which should not have any direct contact with medium 2, in order to prevent corrosion, and, thus, damage. Cover layer 13 can, in the case of manufacture with thick film technology, be a film resistant to the medium, e.g. a film made of a polymer or a ceramic. In the case of manufacture of the sensor in thin film technology, the cover layer 13 is a layer made of silicon oxide, silicon nitride, silicon carbide, etc.

The second reference half cell 6 includes an electrode 10, which is most often represented by a silver/silver chloride electrode. Furthermore, reference half cell 6 includes a supply of electrolyte 11, most often in the form of a potassium chloride solution. Via a liquid junction 12, the supply of electrolyte 11 is in contact with the medium 2. For sensing the potential, the electrode 7 is connected with an electrical line 19.

At least one measuring arrangement 18 is provided, which measures the potentials of the electrodes, respectively the voltages of the component with a sensor effect 4, the first reference half cell 5 and the second reference half cell 6. In the described example of pH measurement, the measuring arrangement 18 represents a voltage measuring device. From the measured voltages (measured variable), the pH value (process variable) is ascertained via a superordinated unit 16 (s.u.) by means of the Nernst equation.

In the contrast to liquid junction 9 of the first reference half cell 5, liquid junction 12 of the second reference half cell 6 is controllable as regards its permeability and its electrolyte flow, i.e. liquid junction 12 can be opened and closed.

Liquid junction 12 is connected via an electrical line 19 with a superordinated unit 16. The superordinated unit 16 can be a microcontroller, a microprocessor, an FPGA, an FPAA, an ASIC, etc. Also, the different functions of the superordinated system 16 can be assumed by a measurement transmitter, etc. Superordinated unit 16 directs and controls the liquid junction 12 in such a manner that the liquid junction is electrolytically permeable in measurement operation.

In FIG. 1, as well as also in FIG. 3 and FIG. 4, the superordinated unit 16 and the measuring arrangement 18 are presented as different components. In FIG. 4, two superordinated units 16 are presented. It is thus possible that each function is assumed by a separate unit. Another option, however, is that the functions are assumed by a single, compact unit. Typically, superordinated unit 16 is not an integral component of electrochemical sensor 1.

Functions of the superordinated unit 16 can be: voltage measurement and/or control of the voltage measurement (for this purpose, in FIG. 1, superordinated unit 16 is connected with measuring arrangement 18), comparison of voltages, reacting to such comparisons, control of the potential sensing lead/leads, data evaluation, data processing, calculating process variables, especially calculating pH value, monitoring process variables, data forwarding, registering events, reacting to events, etc.

Moreover, the superordinated unit 16 can establish the measurement time $t_{1,\,meas}$ and the measuring interval $t_{1,\,int}$ of the first galvanic element 23, as well as also the measurement time $t_{2,\,meas}$ and the measuring interval $t_{2,\,int}$ of the second galvanic element 24. Most often, $t_{2,\,int}$ is greater than $t_{1,\,int}$, and $t_{1,\,meas}$ is equal to $t_{1,\,int}$, i.e. measurements are continuously made at the first galvanic element 23.

In the opened state of liquid junction 12, electrolytic contact exists between the supply of electrolyte 11 and medium 2. In the closed state, no contact exists. Thus, it can be assured that measurement occurs only at certain points in time; for instance, the voltage at the second galvanic element 24 can be measured much less frequently—for instance, once per day—than in the case of the first galvanic element 23.

Figure 2:
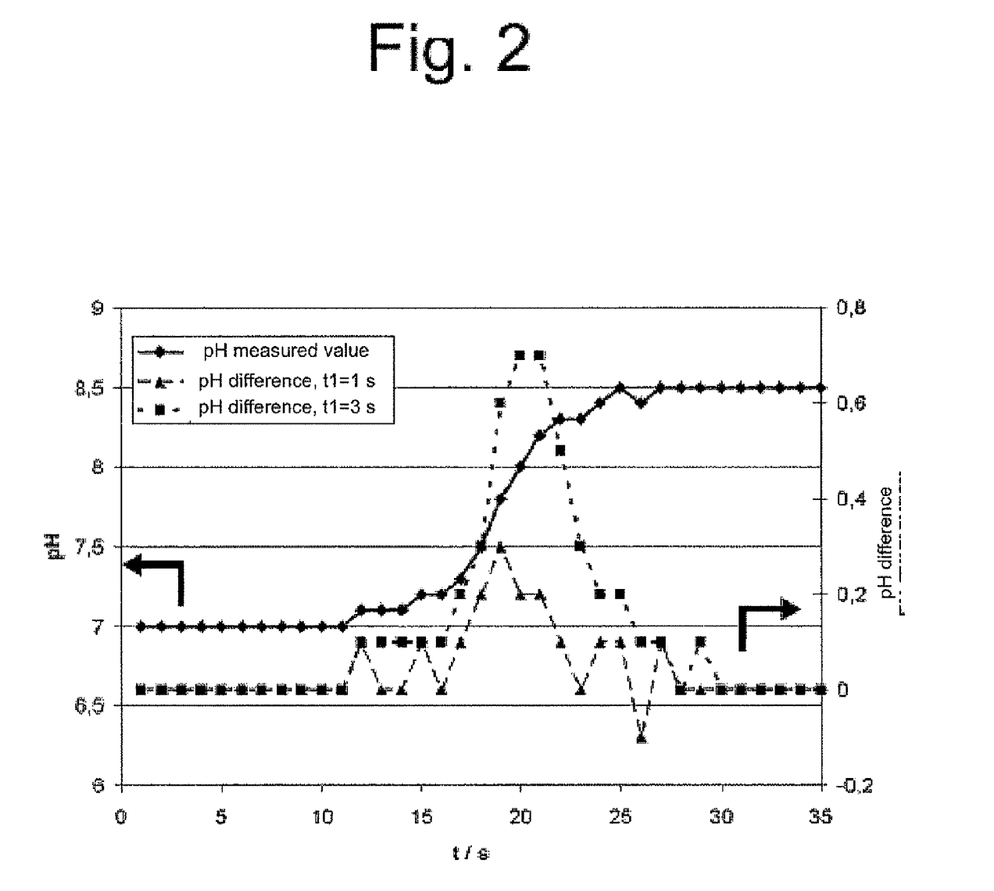

This has advantages: At the first galvanic element 23, the voltage is measured, for example continuously, and thus the pH value is ascertained. In addition to the continuous measuring, a difference pH value is determined, i.e. a past measured value is subtracted from the instantaneous measured value. With the help of this difference value, a change in the measurement can be optimally tracked. FIG. 2 shows such a tracking. In the case of a change in the pH value from 7 to 8.5 within a span of, for instance, 20 s, a peak of the difference measurement occurs to different degrees of strength, depending on different difference time span $t_1$. The highest excursion is received in the example shown in the case of a time span $t_1$ of 3 s. A difference voltage, which is measured above a particular threshold value—in the example, this is 0 V—is detected by the superordinated unit 16 as an "event".

At the second galvanic element 24 with the controllable liquid junction 12, measurements are, as already mentioned much, not made as frequently. Since the liquid junction 12 is opened much less, it can be assumed therefrom that less supply of electrolyte 11 is depleted, and thus this measuring is more accurate. The measured signal can be used as a correction, calibration, adjusting, adapting, etc. for the value at the first galvanic element 23.

By the combination of a continuous measuring with a difference measurement, suddenly occurring events can be optimally detected. The discontinuous measuring durably assures a correct measuring of the process variable.

FIG. 3 shows another embodiment of the sensor of the invention. In such case, the component with sensor effect 4 forms with the first reference half cell 5 the first galvanic element 23. The second galvanic element 24 is formed, in contrast, by the first reference half cell 5 and the second reference half cell 6. Preferably, the reference electrodes 7, 10 are embodied in a low-ohm manner.

FIG. 4 shows a third embodiment of the sensor of the invention. Here, both the liquid junction 12 of the second reference half cell 6 and the liquid junction 17 of the first reference half cell 5 are controllable. Thus, the lifetime of the first reference half cell 5 can also be significantly increased. Attention should be paid that the measuring interval $t_{1,\,int}$ and the difference time span $t_1$ are selected so as to be sufficiently small, so that temporarily occurring events can still be detected.

Furthermore, any combination of the embodiments is possible. Thus, for example, an option is that the liquid junctions of the two reference half cells 5, 6 are controllable, and the second galvanic element 24 is formed from the two reference half cells 5, 6.

Figure 5A:
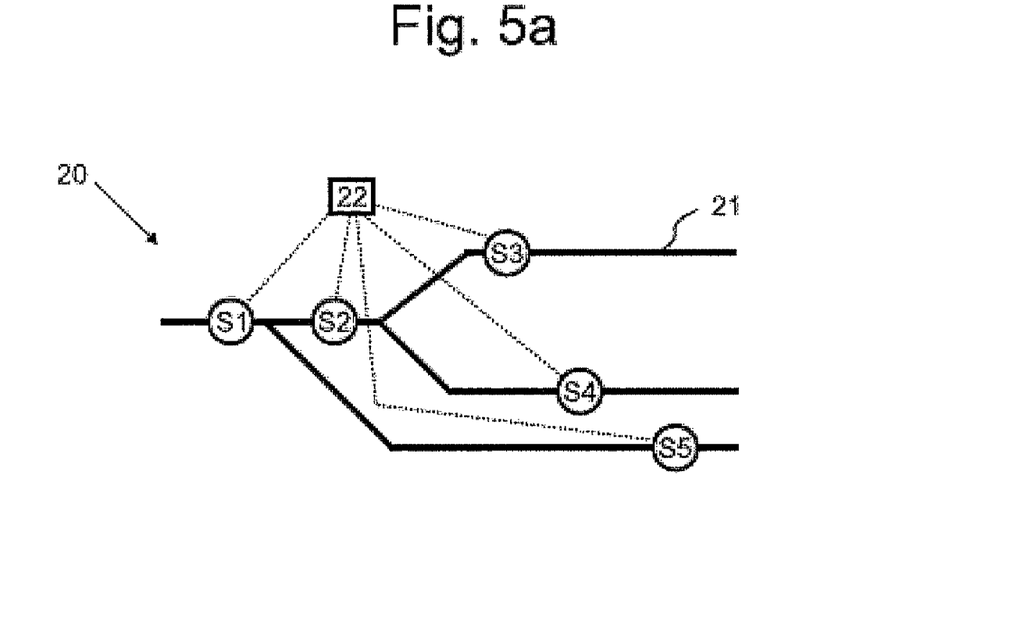

FIG. 5a shows the application of the electrochemical sensor of the invention 1 in a distribution network 20, especially in a water distribution network. The distribution network 20 is composed of waterlines 21. In such case, at least two—in this example, five—sensors S1 to S5 are arranged at different localities within the water distribution network 20.

Sensors S1 to S5 are connected, for instance, via a bus system with a superordinated control unit 22. The superordinated control unit 22 can be a control room or station.

Figure 5B:
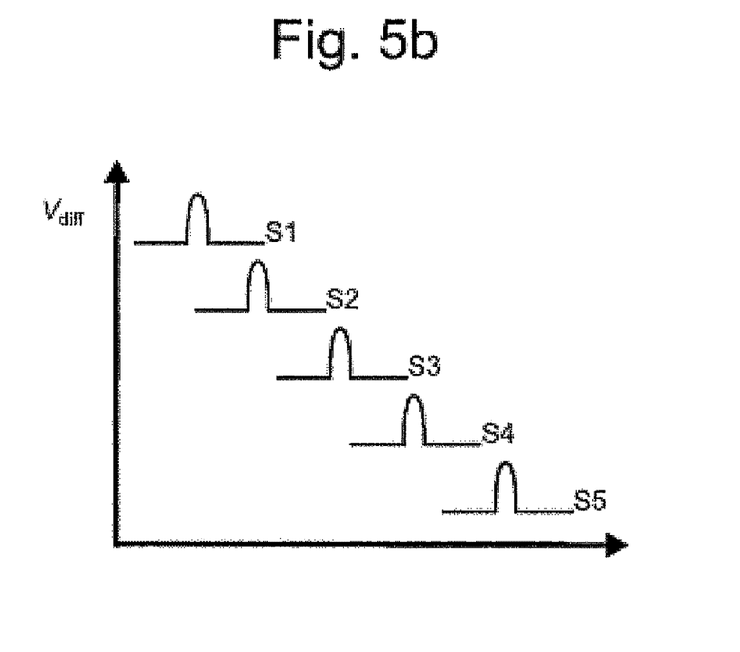

If a sensor S1 registers an event as presented in FIG. 5b, the progression of the event can be traced by the sensors S2 to S5. An option is to register, store and/or log the event. The superordinated control unit 22 then delivers, for example, a corresponding report, in order that the event can be reacted to, for instance, by redirecting the flow of medium via the opening/closing of gates, etc.

The invention claimed is:

1. A method for determining and/or monitoring at least one process variable of a medium by means of at least one electrochemical sensor comprising at least a first reference half cell and a second reference half cell, and comprising the steps of:

measuring a first electrical measured variable $X_{1,\,cont}$ with a first measuring period $t_{1,\,meas}$ and a first measuring interval $t_{1,\,int}$ with reference to the first reference half cell, measuring at least a second electrical measured variable $X_{2,\,discont}$ with a second measuring period $t_{2,\,meas}$ and a second measuring interval $t_{2,\,int}$, taking into consideration the second reference half cell, wherein the second measuring interval $t_{2,\,int}$ is greater than the first measuring interval $t_{1,\,int}$; and determining the at least one process variable from the at least one electrical measured variable $X_{1,\,cont}$ or $X_{2,\,discont}$.

2. The method as claimed in claim 1, wherein:
a difference electrical measured variable $X_{diff}$ is registered, with $$X_{diff}(t=t_0)=X_{1,\,cont}(t=t_0)-X_{1,\,cont}(t=t_0-1),$$

wherein t is time, $t_0$ represents the point in time of the current measured value, and $t_1$ represents a whole numbered multiple of the first measuring interval $t_{1,\,int}$; and
a falling of the difference electrical measured variable $X_{diff}$ below a lower threshold value $X_{1,\,min}$ or a rising of the difference electrical measured variable $X_{diff}$ above an upper threshold value $X_{1,\,max}$ means occurrence of an event, which changes the process variable.

3. The method as claimed in claim 2, wherein:
measurement of the second electrical measured variable $X_{2,\,discont}$ is triggered, when the difference electrical measured variable $X_{diff}$ is determined to lie under the threshold value $X_{1,\,min}$ or over the threshold value $X_{1,\,max}$.

4. The method as claimed in claim 1, wherein:
at least one of the electrical measured variables $X_{1,\,cont}$ or $X_{2,\,discont}$ is ascertained via a potentiometric method;
a component with a sensor effect is provided, which is in contact with the medium;
the first electrical measured variable $X_{1,\,cont}$ is measured relative to the component with the sensor effect; and
the second electrical measured variable $X_{2,\,discont}$ is measured relative to the component with the sensor effect or relative to the first reference half cell.

5. The method as claimed in claim 1, wherein:
at least one of the electrical measured variables $X_{1,\,cont}$ or $X_{2,\,discont}$ is ascertained via an amperometric method; and
an electrode surface is provided, which is embodied as a counterelectrode.

6. An electrochemical sensor for determining and/or monitoring at least one process variable of a medium, comprising:
at least one first reference half cell;
a second reference half cell; and
at least one superordinated unit, wherein:
said first reference half cell determines a first electrical measured variable $X_{1,\,cont}$ with a first measuring period $t_{1,\,meas}$ and a first measuring interval $t_{1,\,int}$;
said second reference half cell determines a second electrical measured variable $X_{2,\,discont}$ with a second measuring period $t_{2,\,meas}$ and a second measuring interval $t_{2,\,int}$;
said second measuring interval $t_{2,\,int}$ is greater than said first measuring interval $t_{1,\,int}$; and
said at least one superordinated unit, ascertains the at least one process variable from at least one electrical measured variable $X_{1,\,cont}$ or $X_{2,\,discont}$.

7. The electrochemical sensor as claimed in claim 6, wherein:
said superordinated unit ascertains a difference electrical measured variable $$X_{diff}, \text{ with } X_{diff}(t=t_0)=X_{1,\,cont}(t=t_0)-X_{1,\,cont}(t=t_0-1),$$

wherein t is time, $t_0$ represents the point in time of the current measured value, and $t_t$ represents a whole numbered multiple of the first measuring interval $t_{1,\,int}$; and
said superordinated unit associates a value of the difference electrical measured variable $X_{diff}$ under a lower threshold value $X_1$ min or over an upper threshold value $X_{1,\,max}$ with an occurrence of an event, which changes the process variable.

8. The electrochemical sensor as claimed in claim 7, wherein:
said superordinated unit triggers measurement of the second electrical measured variable $X_{2,\,discount}$, when it determines that the difference electrical measured variable $X_{diff}$ lies under the threshold value $X_{1,\,min}$ or over the threshold value $X_{1,\,max}$.

9. The electrochemical sensor as claimed in claim 6, wherein:
a component with a sensor effect is provided, which is in contact with the medium;
said first reference half cell ascertains the measured variable $X_{1,\,cont}$ relative to the component with the sensor effect via the potentiometric method; and/or
said second reference half cell ascertains the measured variable $X_{2,\,discont}$ relative to said component with the sensor effect or relative to said first reference half cell via the potentiometric method.

10. The electrochemical sensor as claimed in claim 9, wherein:
said component with a sensor effect is a galvanic half cell, an ion-selective membrane, a semiconductor insulator layer stack, a metal electrode a metal/metal oxide electrode, or a non-metallic redox electrode.

11. The electrochemical sensor as claimed in claim 6, wherein:
said first reference half cell ascertains the measured variable $X_{1,\,cont}$ and/or
said second reference half cell ascertains the measured variable $X_2$, discont via an amperometric method; and
an electrode surface is provided, which is embodied as a counterelectrode.

12. The electrochemical sensor as claimed in claim 6, wherein:
said second reference half cell includes at least one supply of electrolyte and is in contact with the medium via at least a first liquid junction; and
said liquid junction is embodied so as to be controllable and said superordinated unit controls said liquid junction in such a manner that said liquid junction is electrolytically permeable during measurement operation.

13. The electrochemical sensor as claimed in claim 12, wherein:
the control interval of said liquid junction associated with said second reference half cell corresponds to the second measuring interval $t_{2,\,int}$.

14. The electrochemical sensor as claimed in claim 6, wherein:
said first reference half cell includes at least one supply of electrolyte, and is in contact with the medium via at least a second liquid junction;
said at least second liquid junction is embodied so as to be controllable, and said superordinated unit controls said at least second liquid junction in such a manner that said at least second liquid junction is electrolytically permeable during measurement operation; and
the control interval of said at least second liquid junction corresponds to the first measuring interval $t_{1,\,int}$.

15. A system in a distribution network, comprising:
at least two electrochemical sensors;
at least one first reference half cell;
a second reference half cell; and
at least one superordinated unit, wherein:
said first reference half cell determines a first electrical measured variable $X_{1,\,cont}$ with a first measuring period $t_{1,\,meas}$ and a first measuring interval $t_{1,\,int}$;

said second reference half cell determines a second electrical measured variable $X_{2,\,discont}$ with a second measuring period $t_{2,\,meas}$ and a second measuring interval $t_{2,\,int}$;

said second measuring interval $t_{2,\,int}$ is greater than said first measuring interval $t_{1,\,int}$;

said at least one superordinated unit, ascertains the at least one process variable from at least one electrical measured variable $X_{1,\,cont}$ or $X_{2,\,discount}$;

a first electrochemical sensor at a first location registers information, and/or an event, at a first point in time;

a further electrochemical sensor or a number of other electrochemical sensors, which are arranged at least one other location, register such information and/or event at a later point in time; and a superordinated control unit detects propagation of the information and/or of the event and triggers a procedure, a registering, reporting, and/or measure to be taken.

* * * * *